United States Patent [19]

Lewalter et al.

[11] 4,212,982
[45] Jul. 15, 1980

[54] POLYISOCYANATES WITH AT LEAST ONE HYDANTOIN OR THIOHYDANTOIN RING SUBSTITUTED BY CARBOXYLIC ACID AMIDE GROUPS

[75] Inventors: Jürgen Lewalter, Odenthal; Rudolf Merten, Leverkusen; Wilfried Zecher, Leverkusen; Willi Dünwald, Leverkusen, all of Fed. Rep. of Germany

[73] Assignee: Bayer Aktiengesellschaft, Leverkusen, Fed. Rep. of Germany

[21] Appl. No.: 958,690

[22] Filed: Nov. 8, 1978

[30] Foreign Application Priority Data

Nov. 12, 1977 [DE] Fed. Rep. of Germany ....... 2750772

[51] Int. Cl.$^2$ .................. C07D 233/78; C07D 233/86
[52] U.S. Cl. ..................................... 548/313; 528/73; 528/75; 528/902; 521/161

[58] Field of Search ................... 548/308, 313; 528/75

[56] References Cited

U.S. PATENT DOCUMENTS

| | | | |
|---|---|---|---|
| 3,945,982 | 3/1976 | Morgan | 528/75 |
| 3,966,683 | 6/1976 | Merten et al. | 548/308 |
| 4,076,941 | 2/1978 | Sauli | 548/312 |
| 4,091,223 | 5/1978 | Zussman et al. | 548/308 |

Primary Examiner—Natalie Trousof
Assistant Examiner—Jane T. Fan
Attorney, Agent, or Firm—Connolly and Hutz

[57] ABSTRACT

Polyiso(thio)cyanates containing a (thio)hydantoin ring substituted by carboxylic acid amide groups in the molecule are obtained by reacting optionally substituted ethylene- 1,2-dicarboxylic acid anhydrides with amino alcohols and an excess of polyiso (thio) cyanates.

4 Claims, No Drawings

POLYISOCYANATES WITH AT LEAST ONE HYDANTOIN OR THIOHYDANTOIN RING SUBSTITUTED BY CARBOXYLIC ACID AMIDE GROUPS

This invention relates to polyisocyanates with at least one hydantoin or thiohydantoin ring substituted by carboxylic acid amide groups in the molecule, their production by reacting ethylene-1,2-dicarboxylic acid anhydrides, amino alcohols and an excess of polyiso(thio)cyanates, as well as their use in the production of heat-resistant coating agents.

Processes for the production of hydantoins (J. Am. Che. 45/383) and polyhydantoins (Belgian Pat. No. 678,282) are known. The production of hydantoins by the reaction of ethylene-1,2-dicarboxylic acid esters, amines and isocyanates has also been described. However, equivalent amounts of the reactants are generally used in these processes because, when an excess of one reactant is used, in particular of the polyisocyanates, there is a risk of the polyisocyanates forming polyisocyanurates in the presence of the amines instead of the desired hydantoins.

It has surprisingly now been found that, in spite of an excess of polyisocyanates, the production of hydantoins substituted with carboxylic acid amide groups readily takes place and new hydantoin group-containing polyisocyanates are obtained which represent valuable intermediate products.

The invention therefore provides new poly(thio)isocyanates containing (thio)hydantoin groups, preferably those polyiso(thio)cyanates corresponding to general formula (I):

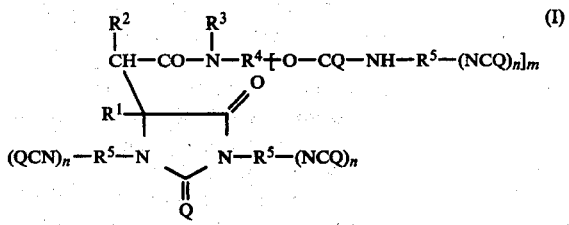

in which
  $R^1$ and $R^2$ are the same or different, and represent optionally substituted aliphatic, aliphatic-aromatic or aromatic radicals, hydrogen or halogen,
  $R^4$ and $R^5$ are the same or different, and represent an at least divalent, optionally substituted aliphatic, aliphatic-aromatic or aromatic radical,
  $R^3$ represents hydrogen, or a monovalent, optionally substituted aliphatic, aliphatic-aromatic or aromatic radical,
  n is an integer of from 1 to 3, preferably 1 to 2, and most preferably 1, and
  m is an integer of 1 or 2, preferably 1 and Q is O or S.

The invention also provides a process for the production of iso(thio)cyanates, which contain (thio)hydantoin rings substituted with carboxylic acid amide groups, by the reaction of optionally substituted ethylene-1,2-dicarboxylic anhydrides with primary or secondary amino alcohols to form the corresponding (isomeric) hemi-amides and the subsequent reaction with polyiso(thio)cyanates, wherein the equivalence ratio of isothiocyanate groups to the hemi-amide of the ethylene dicarboxylic acid amounts to at least 1.1.

The reaction can be represented diagrammatically by the following formula equation.

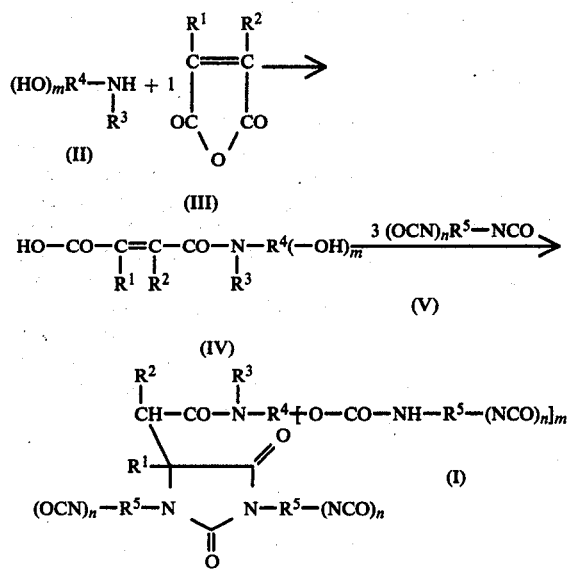

In this formula equation $R^1$, $R^2$, $R^3$, $R^5$, n and m have the meanings given above.

OH-Group-containing hemi-amides of $\alpha,\beta$-unsaturated dicarboxylic acids are used for producing the new polyisocyanates according to the invention and are produced in known manner in situ or in a previous reaction from $\alpha,\beta$-unsaturated 1,2-dicarboxylic acid anhydrides and primary or secondary amino alcohols.

In addition to maleic acid anhydride, halogen or $C_1$–$C_6$ alkyl-substituted ethylene-1,2-dicarboxylic acid anhydrides, preferably methyl, dimethyl, ethyl, butyl or $\Delta^1$-cyclohexane-1,2-dicarboxylic acid anhydrides, can also preferably be reacted with the amino alcohols. $R^1$ and $R^2$ in the general formulae given above are therefore the same or different, and preferably hydrogen, a halogen such as chlorine or fluorine, a $C_1$–$C_6$ alkyl radical or a $C_5$–$C_8$ cycloalkyl radical, a $C_7$–$C_{16}$ alkylaryl radical, or a $C_6$–$C_{20}$ aryl radical, and together can also form a ring with up to 8 ring members. The anhydride of maleic acid is most preferably used.

The hydroxyamino compounds used for preparing the OH-group-substituted hemi-amides can be optionally substituted aliphatic, cycloaliphatic, araliphatic, aromatic or even heterocyclic compounds which contain a primary or secondary amino group in the molecule in addition to at least one hydroxyl group. $R^3$ has the meaning already given above for $R^1$ and $R^2$, with the exception of halogen and can also be substituted with OH-groups when the radical contains 2 or more C-atoms. $R^4$ in the amino-hydroxy compound of the general formula (II) preferably denotes a $C_2$–$C_{10}$ aliphatic radical, a $C_5$–$C_{10}$ cycloaliphatic radical, a $C_7$–$C_{16}$ araliphatic radical, a $C_6$–$C_{20}$ aromatic radical, or a $C_5$–$C_{12}$ aryl or cycloalkyl radical containing at least one heteroatom such as N, O or S. It most preferably denotes a $C_2$–$C_4$ alkyl radical, a $C_5$–$C_{10}$ cycloalkyl radical or a $C_6$–$C_{10}$ aryl radical.

Particularly preferred hydroxyamino compounds include ethanolamine, propanolamine, butanolamine, aminomethylphenol, aminophenol, their N-methyl, N-ethyl or N-butyl derivatives, diethanolamine, dipropanolamine, 1-amino-2,3-propane diol or 1-amino-1,3-propanediol.

The reaction of the hydroxyamino compounds with the ethylene-1,2-dicarboxylic acid anhydrides is generally carried out at temperatures of from −20° C. to 150° C., preferably at 0° C. to 100° C.

Catalysts such as potassium carbonate, trialkylamine, endoethylene piperazine or acetic acid can optionally be used during the addition. In the case of less soluble components or components which melt at higher temperatures, the reaction is generally carried out with advantage in organic solvents of the type which may be used for the subsequent reactions and which are described below. The proportions of $\alpha,\beta$-unsaturated carboxylic acid anhydrides and amino alcohols should advantageously be stoichiometric. Excess proportions of one or other of the components can, however, be used and can be incorporated into the polymers by means of subsequent reactions known per se and not included in the invention.

Instead of the hemi-amides which contain hydroxyl groups and are produced in situ, it is obviously also possible to use isomeric members of this class of substances which have been produced by any methods and have been optionally purified.

Cis/trans-isomerisation can optionally be assisted or achieved by means of heat, bases and/or halogens.

Polyisocyanates to be used according to the invention include aliphatic, cycloaliphatic, araliphatic, aromatic and heterocyclic polyisocyanates (cf. Annalen 562, pages 75 to 136), for example ethylene diisocyanate, 1,4-tetramethylene diisocyanate, 1,6-hexamethylene diisocyanate, 1,12-dodecane diisocyanate, cyclobutane-1,3-diisocyanate, cyclohexane-1,3- and -1,4-diisocyanate as well as any mixtures of these isomers, 1-isocyanato-3,3,5-trimethyl-5-isocyanato-methyl-cyclohexane (German Auslegeschrift No. 1,202,785), 2,4- and 2,6-hexahydrotoluylene diisocyanate as well as any mixtures of these isomers, hexahydro-1,3- and/or -1,4-phenylene diisocyanate, perhydro-2,4'-and/or -4,4'-diphenylmethane diisocyanate, 1,3- and 1,4-phenylene diisocyanate, 2,4- and 2,6-toluylene diisocyanate as well as any mixtures of these isomers, diphenylmethane-2,4'- and/or -4,4'-diisocyanate, naphthylene-1,5-diisocyanate, triphenylmethane-2,2',4''-triisocyanate, polyphenylpolymethylene polyisocyanates, of the type obtained by aniline-formaldehyde condensation and subsequent phosgenation and described for example in British Pat. Nos. 874,430 and 848,671, perchlorinated aryl polyisocyanates of the type described for example in German Auslegeschrift No. 1,157,601, polyisocyanates containing carbodiimide groups of the type described in German Pat. No. 1,092,007, diisocyanates of the type described in U.S. Pat. No. 3,492,330, polyisocyanates containing allophanate groups, of the type described in British Pat. No. 994,890, Belgian Pat. No. 761,626 and published Dutch patent application No. 7,102,524, polyisocyanates containing isocyanurate groups of the type described for example in German Pat. Nos. 1,022,789; 1,222,067 and 1,027,394 as well as in German Offenlegungsschriften Nos. 1,929,034 and 2,004,048, polyisocyanates containing urethane groups of the type described for example in Belgian Pat. No. 752,261 or in U.S. Pat. No. 3,394,164, polyisocyanates containing acylated urea groups according to German Pat. No. 1,230,778, polyisocyanates containing biuret groups of the type described for example in German Pat. No. 1,101,394; in British Pat. No. 889,050 and in French Pat. No. 7,017,514, polyisocyanates produced by telomerisation reactions of the type described for example in Belgian Pat. No. 723,640, polyisocyanates containing ester groups of the type described for example in British Pat. Nos. 956,474 and 1,072,956, in U.S. Pat. No. 3,567,763 and in German Pat. No. 1,231,688, and reaction products of the above-mentioned isocyanates with acetals according to German Pat. No. 1,072,358.

It is also possible to use the distillation residues containing isocyanate groups which are produced during the industrial production of isocyanates, and which are optionally dissolved in one or more of the above-mentioned polyisocyanates. It is also possible to use any mixtures of the above-mentioned polyisocyanates.

Polyisocyanates corresponding to the following general formula are preferably used:

$$R^5(NCO)_{n+1} \qquad (V)$$

in which $R^5$, as in the general formula (I), represents an optionally substituted aliphatic radical with 2 to 20 carbon atoms, an aromatic radical with 5 to 12 carbon atoms, a cycloaliphatic radical with 5 to 12 carbon atoms, an aliphatic-aromatic radical with 6 to 20 carbon atoms or an aromatic or cycloaliphatic radical with 5 to 12 carbon atoms containing at least one hetero atom such as N, O ro S. n is an integer of from 1 to 3, preferably 1 or 2, and most preferably 1.

The radicals can all be substituted by halogen, $C_1$–$C_6$ alkyl groups and/or $C_6$–$C_{16}$ aryl groups.

The following are preferably used: commercially readily available mixtures of toluylene diisocyanates, m-phenylenediisocyanate, as well as phosgenated condensates of aniline and formaldehyde with a polyphenylene-methylene structure, and the symmetrical compounds 4,4'-diisocyanatodiphenylmethane, 4,4'-diisocyanatodiphenylether, p-phenylene diisocyanate and 4,4'-diisocyanatodiphenyl dimethyl methane, isophorone diisocyanate as well as 4,4'-diisocyanatodiphenyl sulphide and hexamethylene diisocyanate.

The isocyanates can be used in free form, or partly or completely also in the form of their derivatives which can be obtained by reaction with compounds containing reactive hydrogen and which react as isocyanate-releasing compounds under the reaction conditions.

The isocyanate-releasing compounds are preferably carbamic acid esters obtained from aromatic and aliphatic mono- and polyhydroxy compounds and the addition products obtained from lactams, oximes and CH—acidic compounds.

Examples include the carbamic acid esters of phenol, isomeric cresols, their commercial mixtures and similar aromatic hydroxyl compounds, aliphatic monoalcohols such as methanol, ethanol, propanol, isopropanol, butanol, isobutanol, cyclohexanol, allyl alcohol, benzyl alcohol, and aliphatic diols or polyols such as ethylene glycol and trimethylol propane, and also the addition products with pyrrolidone-(2), caprolactam, butanone-oxime, malonic ester, acetoacetic ester and acetophenone. The monoethers of ethylene and diethylene glycol or propylene and dipropylene glycol with methanol, ethanol, butanol, benzyl alcohol or phenols are also suitable.

The isocyanate-releasing compounds can be used as such or be produced in situ by reaction with the corresponding reactants.

The analogous (poly)-isothiocyanates can also be used as starting materials instead of the above-mentioned (poly)isocyanates.

The proportions of hemi-amides containing OH—groups and polyiso(thio)isocyanates have to be selected in such a way that the reaction products obtained contain excess iso(thio)cyanate groups, as far as possible above 10%, preferably above 30%, optionally in masked form. For this purpose it is necessary for the equivalence ratio of iso(thio)cyanate groups to the hemi-amides to amount to at least 1.1. This means than more than 3 equivalents of iso(thio)cyanate groups of the polyiso(thio)cyanate component to be added must for example be used per mol of hemi-amide with one alcoholic OH-group, though excess polyiso(thio)cyanate used does not interfere and can optionally be removed later on or even left as additional polyiso(thio)cyanate in the reaction product.

The reaction according to the invention between the hemi-amides containing hydroxy groups and the polyisocyanates to form the claimed polyisocyanates containing polyhydantoin groups optionally takes place in solvents which are inert towards the reactants or are capable of reacting with the polyisocyanate component to form addition compounds, for example phenols, lactams, alcohols, hydrocarbons, halogenated hydrocarbons, esters, cyclic esters, ketones, ethers, substituted amides and nitriles. These include, for example, phenol, commercial cresol mixtures, $\epsilon$-caprolactam, acetophenone, ethylene glycol butyl ether, diethylene glycol methyl ether, cyclohexanone, glycolmonomethyl ether acetate, $\gamma$-butyrolactone, $\epsilon$-caprolactone, benzoic acid alkyl ester, N-methylpyrrolidone, dimethylformamide, dimethylacetamide, benzonitrile and others as well as their mixtures.

In order to react the hemi-amides with the polyiso(thio)cyanates, the reactants, optionally will the solvents, are kept for a few minutes to several hours at temperatures of from $-20°$ C. to $350°$ C., preferably $0°$ C. to $250°$ C. The progress of the reaction can be followed by means of the IR-spectrum.

The high velocity of the reaction according to the invention allows it also to be carried out in the presence of phenolic and/or alcoholic hydroxyl groups and/or amide groups. This means that groups of this type can be present throughout in the reactants or as blocking agents and as solvent like an excess of hydroxyl or lactam components.

This reaction can optionally be carried out under inert gas.

The acidity of acidic solvents such as phenols or cresols is sufficient for the reaction to be completed within a sufficiently short time. In inert media or in solvent-free reaction mixtures, carboxylic acids with a sufficiently high melting point or boiling point, for example, such as acetic acid, benzoic acid, succinic acid, benzodicarboxylic acids, butane tetracarboxylic acid, trimellitic acid or their anhydrides, may also be used as catalysts which become chemically fixed in the reaction products. They may be added in amounts of 0.1 to 40, preferably 1 to 10% in val, based on 1 val of polyiso(thio)cyanate.

In order to accelerate further the reactions suitable bases, acids and/or metal catalysts which are known from isocyanate chemistry such as triethylamine, N-methylmorpholine, endoethylenepiperazine, titanium tetrabutylate, titanium aminoalcoholate, iron acetylacetonate, dibutyltin dilaurate, lead octoate, acetic acid or p-toluenesulphonic acid may be used.

As already mentioned, the reaction according to the invention can also be caried out in situ from the individual components, i.e. the amino alcohols, the $\alpha,\beta$-unsaturated 1,2-dicarboxylic acid anhydrides and the polyiso(thio)cyanates, in one reaction step. Another variation of the process involves a sequence of reactions which takes place in such a way that the primary addition products obtained from the amino alcohol component and the polyiso(thio)cyanates are converted into the polyiso(thio)cyanates containing the hydantoin groups according to the invention by addition of the $\alpha,\beta$-unsaturated 1,2-dicarboxylic acid anhydride.

The polyiso(thio)cyanates containing substituted hydantoin groups according to the invention represent high-viscous to brittle compositions which can be applied in concentrated form or even as solutions in the solvents already mentioned above, depending upon their application.

The polyiso(thio)cyanates containing substituted (thio)hydantoin groups according to the invention are used for the production of polyurethane plastics, preferably for electrical insulating materials. In this application, the polyisocyanates according to the invention can be stoved directly by known methods with conventional polyesters, polyester imides, polyamide imides, polyester amide imides or polyester hydantoins to form carbamic ester structures. Another application of the inventive polyisocyanates in their use as polyisocyanate components in the conventional process for the production of polyimides, polyamide imides and polyhydantoins optionally containing ester groups. This reaction can be carried out both in a preliminary stage and in situ together with the stoving process. The modes of operation adopted for this purpose are disclosed for example in Belgian Pat. No. 678,282 (=U.S. Pat. No. 3,397,253) and German Pat. No. 1,035,362 (=U.S. Pat. No. 2,952,665).

EXAMPLE 1

522.6 g of toluylene diisocyanate (mixture of 2,4:2,6 isomers in ratio of 80:20) are dissolved under $N_2$ in 100 g of acetophenone, combined at $20°$ to $150°$ C. in portions with the anhydride-free mixture produced previously under $N_2$ at 5 to a maximum of $70°$ C. from 98.1 g of maleic acid anhydride, 402 g of Carbitol (diethylene glycol monoethyl ether), 12 g of $\epsilon$-caprolactam and 75 g of N-methylaminoethanol, subsequently stirred for one hour at $70°$ C., reacted with 0.5 g of Endoethylene piperazin and stirred at above $100°/120°$ C. to $150°$ to $160°$ C. for above five hours until $CO_2$ evolution, which was initially quite vigorous, has ended and the NCO groups have been used up, and subsequently tempered at $175°$ C. and $200°$ to $210°$ C. for a further 0.5 hours at each temperature. The mixture is then reacted at $120°$ to $140°$ C. with a total of 384.2 g of trimellitic acid anhydride, 166.1 g of isophthalic acid, and 388.4 g of terephthalic acid dimethyl ester, is homogenised during $CO_2$ evolution by slow heating at above $150°/170°$ C. to $200°$ C. and condensed for about three hours or until the end of $CO_2$ evolution at $200°$ to $210°$ C. 276.3 g of glycerine and 1.0 g of butyl titanate are then added at $120°$ C. to $130°$ C. and the mixture is condensed again for above five hours at $200°$ to $220°$ C. and finally for about one hour under vacuum at $200°$ to $210°$ C. The mixture is subsequently diluted at $150°$ to $120°$ C. with 1470 g of acetophenone, reacted with the solution of 16 g of titanium tetrabutylate in 32 g of acetyl acetone and homogenised for a further hour at 120° to 100° C.

The lacquer solution having a solid content of 50% has a viscosity of 7300 cP$_{20°\ C.}$.

The 0.7 mm copper wire coated with this wire lacquer in a 4 m furnace at 9 m per minute has a softening temperature of greater than 330° C., a heat shock resistance of greater than 240° C. and a lasting heat endurance of about 14 days at 200° C.

EXAMPLE 2

44.1 g of maleic acid anhydride in 500 g of γ-butyrolactone are heated for about one minute to 100° C., then reacted at 20° C. under $N_2$ with 33.8 g of N-methylamino ethanol, subsequently stirred for about one hour at 70° C. until the anhydride groups are consumed and then mixed at 30° C. with 298.9 g of N,N'-bis[2-methoxycarbonylpropyl-(2)]-4,4'-diamino-diphenylmethane and homogenised. This solution is then reacted at 30° to 45° C. with a solution of 500.4 g of 4,4'-diisocyanatodiphenyl methane and 200 g of toluene, the mixture is stirred for about three hours at 20° C. to 35° C., homogenised at 50° to 75° C. with 153.7 g of trimellitic acid anhydride and 132.9 g of isophthalic acid, 0.5 g of Endoethylenpiperazin are added and the mixture is condensed for above five hours at 200° C. The mixture is subsequently reacted at 120° C. with 194.1 g of terephthalic acid dimethyl ester and 184.0 g of glycerine as well as 1.0 g of butyl titanate, heated above 140° to 150° C. for about six hours to 200° to 220° C. and finally after-condensed for about one more hour under vacuum at 200° to 210° C. The mixture is then diluted at 150° to 120° C. with 1011 g of benzoic acid methyl ester, is reacted with a solution of 13 g of titanium tetrabutylate in 26 g of acetyl acetone and is homogenised for about one more hour at 100° to 120° C.

The 50% lacquer solution has a viscosity of 3800 cP 20° C.

The 0.7 mm lacquered copper wire produced in a 4 m furnace at 8 m per minute has a softening temperature of greater than 330° C., a heat shock resistance of greater than 260° C., a lasting heat endurance of more than seven days at 200° C., a scraping-fastness of 109 double strokes, a dielectric strength of 9 kV as well as good resistance to chemicals.

EXAMPLE 3

1501.2 g of 4,4'-diisocyanatodiphenyl methane are combined under $N_2$ at 50° to 150° C. in portions with a solution which has previously been produced under $N_2$ at 5 to a maximum of 30° C. from 196 g of maleic acid anhydride in 844 g of Carbitol, 21 g of ε-caprolactam and 150 g of ω-aminopropanol, the mixture is stirred at 150° C. until the end of the $CO_2$ evolution, which was initially very vigorous, and is finally stirred under reflux conditions for about 0.5 hours at 200° to 220° C.

The brownish-black homogeneous resin with the typical hydantoin IR-bands has a latent NCO content of about 9.4% (theoretically : 30%) and a 70% solution in Carbitol has a viscosity of about 11570 cP 20° C.

EXAMPLE 4

324 of a commercial cresol mixture are introduced dropwise into a solution of 750 g of 4,4'-diisocyanatodiphenyl methane in 600 g of butyrolactone at 110° to 120° C. according to the evolution of heat. The mixture is then stirred for a further 0.5 hours at 120° C. The mixture is subsequently cooled to 0° C. and 473 g of a 31% solution of N-hydroxyethyl-N-methyl-maleic acid amide in butyrolactone, which has been produced from N-methyl-ethanolamine and maleic acid anhydride, are introduced into the mixture with cooling a this temperature. The mixture is then stirred for one hour each at 10°, 20°, 30°, 50° and 75° C. and for six hours at 100° C. Condensation takes place with elimination of carbon dioxide. After the addition of 11 g of cresol, the isocyanato-hydantoin is obtained as a brown viscous solution having a viscosity of $\eta^{25}=83,000$ mPa s. The content of masked isocyanate amounts to 6.5%.

A lacquer solution is prepared from 100 g of this solution with 150 g of a polyester formed from teraphthalic acid, ethylene glycol and glycerine, 400 g of cresol and 1 g of titanium tetrabutylate, and the lacquer solution is painted on a sheet of metal and stoved for 15 minutes each at 200° C. and 300° C. to form a clear elastic lacquer film.

EXAMPLE 5

255 g of a commercial cresol mixture, 31 g of ethylene glycol and 105 g of the solution produced according to Example 4 of an isocyanato-hydantoin are taken and reacted at 120° C. firstly with 70 g of a mixture of 80 parts 2,2- and 20 parts 2,6-toluylene-diisocyanate and then with 195 g of trimellitic acid anhydride. The mixture is stirred for condensation, which takes place with elimination of carbon dioxide and water, for two hours each at 170° C., 180° C., 190° C., 200° C. and 205° C. The hydantoin ester imide is obtaned as a brown viscous solution which is diluted with equal parts of phenol and cresol to a solids content of 40%, of which the viscosity then amounts to $\eta^{25}=14300$ mPa s.

In order to prepare a lacquer solution, 250 g of a polyester formed from terephthalic acid, ethylene glycol and glycerine and 7.5 g of titanium tetrabutylate as catalyst are added and diluted with cresol to a solids content of 30%.

A 0.7 mm diameter copper wire is lacquered with this solution in a wire lacquering machine.
Furnace length: 4 m
Furnace temperature: 400° C.
Number of passages through furnace: 6.

A coated wire with a maximum external fibre elongation of 88% and a heat shock resistance of 260° C. is obtained at a wire draw-off rate of 11 m per minute under these conditions.

EXAMPLE 6

222 g of n-butanol are introduced dropwise into a solution of 750 g of 4,4'-diisocyanato-diphenylmethane in 600 g of butyrolactone at 90° C. with cooling. The mixture is then cooled to 0° C. and 473 g of a 31% solution of N-hydroxy-ethyl-N-methyl-maleic acid amide in butyrolactone are added in portions. The mixture is then stirred for one hour each at 10°, 20°, 30° and 50° C. and ten hours at 100° C. in order to effect condensation and cyclisation. Upon completion of the reaction, a further 7.4 g of n-butanol are stirred in and a solution of the butanol-masked isocyanato-hydantoin is obtained, the free-isocyanate content of which is less than 0.5%.

200 g of this solution are reacted with 100 g of a polyester formed from terephthalic acid, glycol and glycerine and 1 g of titanium tetrabutylate, diluted with cresol to a solids content of 30% and applied to a 0.7 mm diameter copper wire under the conditions described in Example 2. A lacquered wire with a softening temperature of 309° C. and an abrasion resistance of 26 strokes is obtained.

EXAMPLE 7

324 g of a commercial cresol mixture are introduced dropwise into a solution of 522 g of a mixture of 80 parts of 2,4- and 20 parts of 2,6-toluylene diisocyanate at 110° to 120° C. The mixture is then stirred for a further hour at this temperature. It is then cooled and 473 g of a 31% solution of N-hydroxyethyl-N-methyl-maleic acid amide in butyrolactone are added dropwise at 0° C. The temperature of the reaction mixture is raised with stirring to 100° C. within six hours and then kept at 100° C. for two hours, 110° C. for one hour and 120° C. for one hour. The cresol-masked isocyanato-hydantoin is obtained as a brown viscous solution, which is used to prepare a lacquer solution by mixing with a polyester formed from terephthalic acid, glycol and glycerine in a ratio of 1:2, reacting with 1% titanium tetrabutylate and diluting with cresol to a solids content of 30%.

Lacquering of a 0.7 mm diameter copper wire with this solution under the conditions described in Example 2 produces a lacquered wire with a softening temperature of 318° C. at a draw-off rate of 7 m per minute.

EXAMPLE 8

255 g of butyrolactone, 31 g of ethylene glycol and 130 g of an isocyanato-hydantoin produced in accordance with Example 4 are taken and reacted at 120° C. in portions with 70 g of a mixture of 80 parts of 2,4- and 20 parts of 2,6-toluylene diisocyanate. 192 g of trimellitic acid anhydride are then added and condensation is carried out with stirring for two hours each at 170°, 180°, 190°, 200° and 205° C. The hydantoin ester imide is obtained as a brown viscous solution. The viscosity $\eta^{25}$ of a solution diluted with cresol to a solids content of 40% amounts to 2340 mPa s.

In order to prepare a lacquer solution, 200 g of the reaction product are reacted with 100 g of a polyester formed from terephthalic acid, glycol and glycerine and 3 g of titanium tetrabutylate, and diluted with equal portions of phenol and cresol to a solids content of 30%. This lacquer solution is applied to a 0.7 mm diameter copper wire, as described in Example 2. A lacquered wire with a maximum external fibre elongation of 88% and a heat shock resistance of 260° C. is obtained at a wire draw-off rate of 9 m per minute.

EXAMPLE 9

222 g of n-butanol are introduced dropwise with cooling into a solution of 522 g of 2,4-toluylene diisocyanate in 675 g of butyrolactone at 110° C. The mixture is then cooled to 0° C. and 473 g of a 31% solution of N-hydroxyethyl-N-methyl-maleic acid amide are introduced into it. The temperature is then raised by 10° C. per hour to 100° C. with stirring and then kept for a further two hours at 100° C. and for two hours at 120° C. The butanol-masked isocyanato-hydantoin is obtained as a brown viscous solution having a free isocyanate content of less than 0.4%.

A sample is reacted in a proportion of 1:1 with a polyester formed from terephthalic acid, glycol and glycerine and with 1.5% of titanium tetrabutylate, and diluted with cresol to a solids content of 30%. The lacquer solution is painted on a sample of sheet metal and produces a clear elastic lacquer film after stoving for 15 minutes each at 200° and 300° C.

We claim:

1. A polyiso(thio)cyanate containing a (thio)hydantoin group of the formula $$\begin{array}{c} R^2 \quad R^3 \\ | \quad\quad | \\ CH-CO-N-R^4+O-CQ-NH-R^5-(NCQ)_n]_m \\ R^1 \quad\quad\quad O \\ \\ (QCN)_{\overline{n}}-R^5-N \quad\quad N-R^5-(NCQ)_n \\ \| \\ Q \end{array}$$

wherein
$R^1$ and $R^2$ are the same or different and each is alkyl having 1-6 carbon atoms, cycloalkyl having 5-8 carbon atoms, alkylaryl having 7-16 carbon atoms, aryl having 6-20 carbon atoms, halogen or hydrogen and when $R_1$ and $R_2$ together form a ring, said ring has up to 8 ring members;
$R^3$ has the same meaning as $R^1$ and $R^2$ except that $R^3$ may not be halogen and may be additionally substituted by hydroxyl when containing two or more carbon atoms;
$R^4$ is alkyl having 2-10 carbon atoms, cycloalkyl having 5-10 carbon atoms, alkylaryl having 7-16 carbon atoms or aryl having 6-20 carbon atoms;
$R^5$ is alkyl having 2-20 carbon atoms, cycloalkyl having 5-12 carbon atoms, alkylaryl having 6-20 carbon atoms or aryl having 5-12 carbon atoms all of which are unsubstituted or substituted by halogen;
Q is oxygen or sulfur;
n is an integer from 1-3; and
m is 1 or 2.

2. A polyisocyanate as claimed in claim 1, wherein Q represents oxygen.

3. A polyiso(thio)cyanate as claimed in claim 1, wherein n represents 1 or 2.

4. A polyiso(thio)cyanate as claimed in claim 1, wherein m represents 1.

* * * * *